(12) United States Patent
Garito et al.

(10) Patent No.: US 7,101,370 B2
(45) Date of Patent: Sep. 5, 2006

(54) DISPOSABLE ELECTROSURGICAL HANDPIECE FOR TREATING TISSUE

(76) Inventors: Jon C. Garito, 3333 Royal Ave., Oceanside, NY (US) 11572; Alan G. Ellman, 3333 Royal Ave., Oceanside, NY (US) 11572

( * ) Notice: Subject to any disclaimer, the term of this patent is extended or adjusted under 35 U.S.C. 154(b) by 201 days.

(21) Appl. No.: 10/866,630

(22) Filed: Jun. 14, 2004

(65) Prior Publication Data

US 2005/0277917 A1    Dec. 15, 2005

(51) Int. Cl.
*A61B 18/18*    (2006.01)
(52) U.S. Cl. .............................. 606/41; 606/46; 606/51
(58) Field of Classification Search ............ 606/41–52, 606/205, 206
See application file for complete search history.

(56) References Cited

U.S. PATENT DOCUMENTS

| | | | |
|---|---|---|---|
| 5,919,191 A | 7/1999 | Lennox et al. | |
| 6,231,570 B1 | 5/2001 | Tu | |
| 6,231,571 B1 * | 5/2001 | Ellman et al. | 606/41 |
| 6,428,538 B1 | 8/2002 | Blewett et al. | |
| 6,530,924 B1 * | 3/2003 | Ellman et al. | 606/45 |
| 2005/0107779 A1 | 5/2005 | Ellman et al. | |

FOREIGN PATENT DOCUMENTS

| | | |
|---|---|---|
| DE | 43 37 590 A1 | 11/1994 |
| FR | 2 355 521 | 1/1978 |

* cited by examiner

*Primary Examiner*—Michael Peffley

(57) ABSTRACT

A disposable or reusable bipolar or unipolar electrosurgical handpiece having an extendable and retractable active electrode end and housed in a relatively inexpensive body comprising an actuating handle for use in various electrosurgical procedures. The housing comprises slidable body sections with one of the sections having an internal structure configured for receiving an incoming wire whose stripped end or ends can be contacted to the active electrode end by way of an externally-exposed electrically-conductive band on the electrode.

10 Claims, 8 Drawing Sheets

DISPOSABLE ELECTROSURGICAL HANDPIECE FOR TREATING TISSUE

RELATED APPLICATIONS

U.S. application Ser. No. 09/303,839, filed May 3, 1999, commonly owned, for "Electrosurgical Handpiece For Treating Tissue", now U.S. Pat. No. 6,231,571.

U.S. application Ser. No. 09/393,286, filed Sep. 10, 1999, commonly owned, for "Electrosurgical Handpiece For Treating Tissue", now U.S. Pat. No. 6,210,409.

U.S. application Ser. No. 09/483,994, filed Jan. 18, 2000, commonly owned, for "Electrosurgical Handpiece For Treating Tissue", now U.S. Pat. No. 6,352,533.

This invention relates to an electrosurgical handpiece and an activator for an electrosurgical handpiece.

BACKGROUND OF THE INVENTION

Our prior application Ser. No. 09/303,839, describes a novel electrosurgical handpiece for treating tissue in a surgical procedure commonly known as minimally invasive surgery (MIS). Among the features described and claimed in the prior application is an electrosurgical handpiece that can be used in MIS and reduces the danger of excessive heat causing possible patient harm. This is achieved in one embodiment by an electrosurgical handpiece that is bipolar in operation and that is configured for use in MIS. The bipolar operation confines the electrosurgical currents to a small active region between the active ends of the bipolar electrode and thus reduces the possibility that excessive heat will be developed that can damage patient tissue. Moreover, the position of the active region can be controlled to avoid patient tissue that may be more sensitive to excessive heat. Preferably, the handpiece is provided with a dual compartment insulated elongated tube, each of the compartments serving to house one of the two wires of the bipolar electrodes. The electrode for MIS use is preferably constructed with a flexible end controllable by the surgeon so as to allow the surgeon to manipulate the end as desired during the surgical procedure. In a preferred embodiment, the flexible end is achieved by weakening at the end the housing for the electrode, and providing a pull string or wire connected to the weakened housing end and with a mechanism at the opposite end for the surgeon to pull the string or wire to flex the housing end to the desired position. This feature allows the surgeon to position the active electrode end at the optimum location for treating, say, a herniated disk to remove undesired regions and to provide controlled heat to shrink the tissue during surgery. In FIGS. 3–7 of the prior application, a suitable bipolar electrode is described, which comprises a pair of rounded electrodes with spaced flat sides separated by an insulating layer. FIGS. 8–10 illustrate a suitable unipolar electrode construction of the flexible end handpiece. FIG. 12 illustrates how such an electrode can be used for the reduction of herniated disks in a laparoscopic procedure. FIG. 19 shows a construction that combines both a bipolar and a unipolar electrode either of which can be selected by the surgeon for use with the procedure. FIG. 20 shows a scissors end that can be constructed as a bipolar electrode for certain purposes. Other constructions to provide easier flexing of the handpiece end, as well as the use of memory metals to control the position of the extended electrode are also discussed.

Our prior application Ser. No. 09/393,286, describes a modified bipolar electrode construction using the flexible end handpiece, the modified bipolar electrode having spaced prongs.

Our prior application Ser. No. 09/483,994, describes a modified bipolar electrode construction using the flexible end handpiece, the modified bipolar electrode having spaced loops.

One limitation of the handpiece constructions described in these prior applications is the relatively high fabrication costs, which deters single uses of the handpiece by the surgeon. Nowadays, surgeons prefer if feasible disposable instruments that can be discarded after one use and no longer need sterilization and sterile packaging for future uses.

SUMMARY OF THE INVENTION

The present invention continues the teachings of the three prior applications and hereby incorporates by reference the total contents of the three prior applications, Ser. Nos. 09/303,839, 09/393,286, and 09/483,994. The present invention describes and claims among other things a relatively inexpensive handpiece construction for such instruments with flexible tips. Since the present application otherwise makes use of the same teachings of the prior applications, it was felt unnecessary to repeat in the body of this specification many of the details present in the contents of the prior application. The present description will be confined solely to the modifications in the handpiece construction that allow for inexpensive fabrication and hence disposability if desired but which can still use most if not all of the features described in the incorporated applications yet which will still achieve the same benefits as with the constructions of the prior applications. More specifically, the construction of the present invention can provide both bipolar and unipolar operation separately or in the same handpiece, and can use the same constructions described in the prior applications for providing the extendable and retractable straight and/or curved active electrode tips, as well as many of the details for providing a flexible end or a straight end with a curved extendable electrode, including use in the various medical procedures described in the prior applications and known to others in this art in which electrosurgical currents are used to modulate patient tissue, meaning to cut, ablate, shrink, and/or coagulate tissue. For more details, the reader is directed to the prior applications.

The new handpiece constructions of the present improvement are focused for the most part at the gun or handle end of the handpiece, meaning the part of the handpiece held in the hand of the surgeon and operable by the surgeon to extend and retract the flexible tip.

In a preferred embodiment, the handle end of the handpiece is constructed preferably of known plastics, and thus can be, for example, molded in several parts and simply assembled by being force-fitted and/or adhered together by suitable adhesives, or snapped together as is well known in the art for assembling plastic members. Preferably, all parts of the handle end except for electrical terminals, optionally a metal spring, and the electrode assembly are made of inexpensive plastic.

In accordance with another preferred embodiment, the electrical terminal(s) is or are provided by an electrical wire having one or more stripped ends extending into and around a contact member and being at the contact member in surface contact with one or more exposed electrically-conductive surfaces of the electrode. In this preferred embodiment, assembly of the structure establishes the desired permanent contact of the incoming electrical wire to the active electrode.

In a further preferred embodiment, the handle is a one-piece member connected across slidable body parts configured such that squeezing of the handle by the surgeon causes the body parts to come together which action causes the active end of the electrode to extend out of a supporting tube.

The constructions of the invention will provide the same important benefits not only for MIS of herniated disks but also for other MIS procedures where controlled electrode position and/or controlled heat generation is of importance as described in the prior applications, as well as for general electrosurgical procedures where the volumetric reduction of tissue is desirable.

While the invention of the handpiece of the invention has focused on low-cost fabrication allowing disposability or one-time use, it will be understood by those skilled in this art that the same handpiece can also be reusable if the practitioner so desires, by appropriate sterilization after each use. Most forms of sterilization can be used by an appropriate choice of handpiece materials, such as high-temperature plastics, but gas sterilization as is well known in this art can also be used if heat-sensitive material may be present.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similarly functioning parts.

DETAILED DESCRIPTION OF THE PREFERRED EMBODIMENTS

The reader is directed to the referenced prior applications for a more detailed description of the prior applications which will assist in understanding the improvements offered by the present application.

In the present application, the electrode configuration remains essentially the same. It can comprise the use of a pulling wire to flex a flexible end of an outer tube housing for the electrode while simultaneously extending the electrode from the end of the outer tube. Or, preferably, the outer tube end is not flexible, but the electrode distal end 116 is constituted of memory metal or has been given a pre-bent contour such that, when extended from its outer tube housing 18, it assumes a preset curved or straight position that allows the surgeon to reach with the active end of the electrode patient sites behind, say, other tissues more easily. Other electrode constructions that allow the surgeon to extend an active electrode end from an elongated tubular member and cause the active electrode end to assume straight or curved configurations are also considered within the scope of the present invention.

Figure 1:
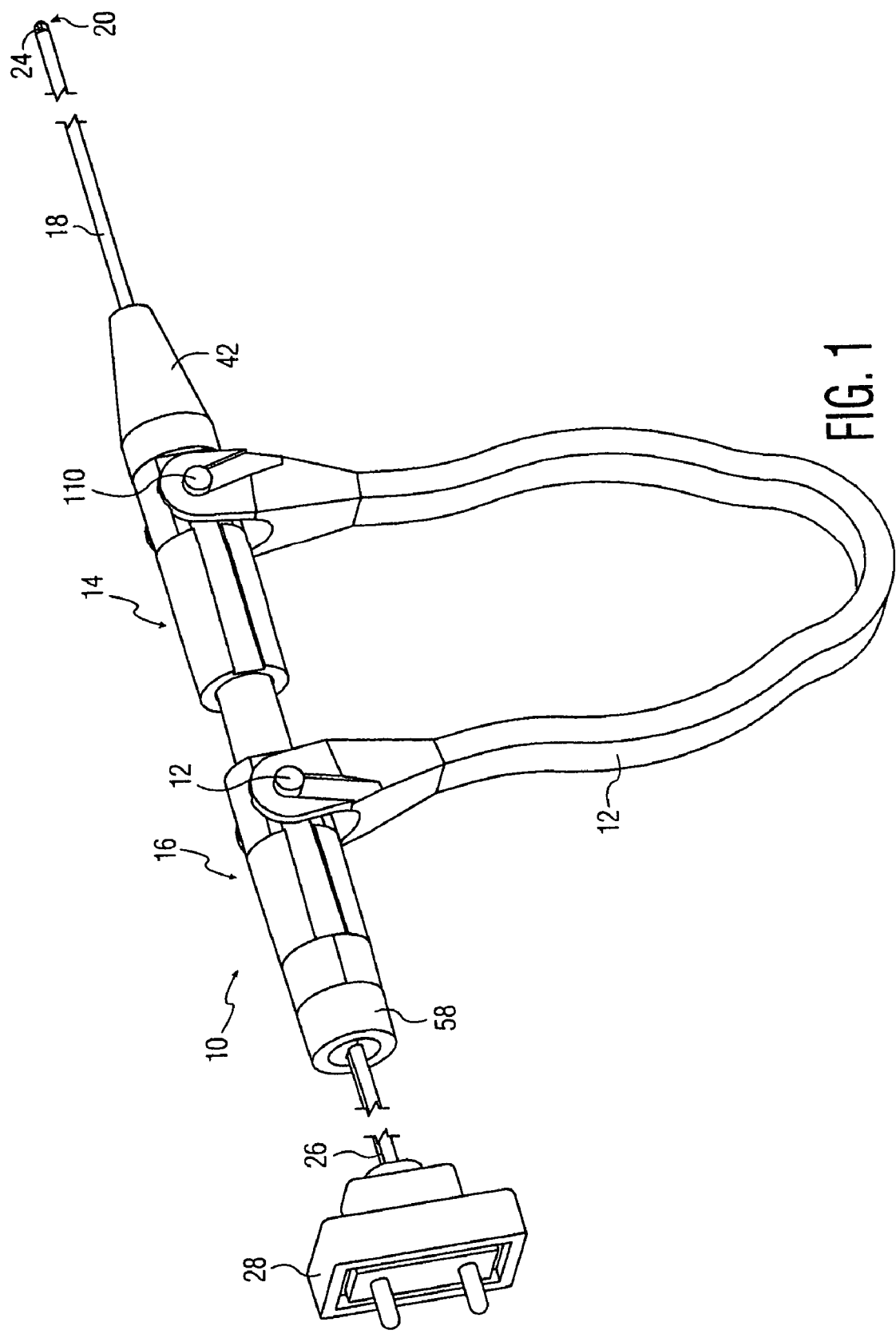
FIG. 1 is a perspective view of one form of electrosurgical handpiece in accordance with the invention with the working end shown in its retracted position.

FIG. 1 shows one form of electrosurgical handpiece 10 of the invention. It comprises a squeezable handle 12 connected to and across two front 14 and rear 16 main slideable body parts enclosing an elongated outer tubular housing 18 from whose distal end 20 an inner electrode 22 with adjacent active bipolar tips 24 can be extended and retracted when the handle 12 is squeezed or released, respectively. At the left end an electrical cord 26 is terminated in a plug connector 28. Internally of the handpiece, wires of the electrical cord 26 are connected to the active electrode 22.

Figure 2:
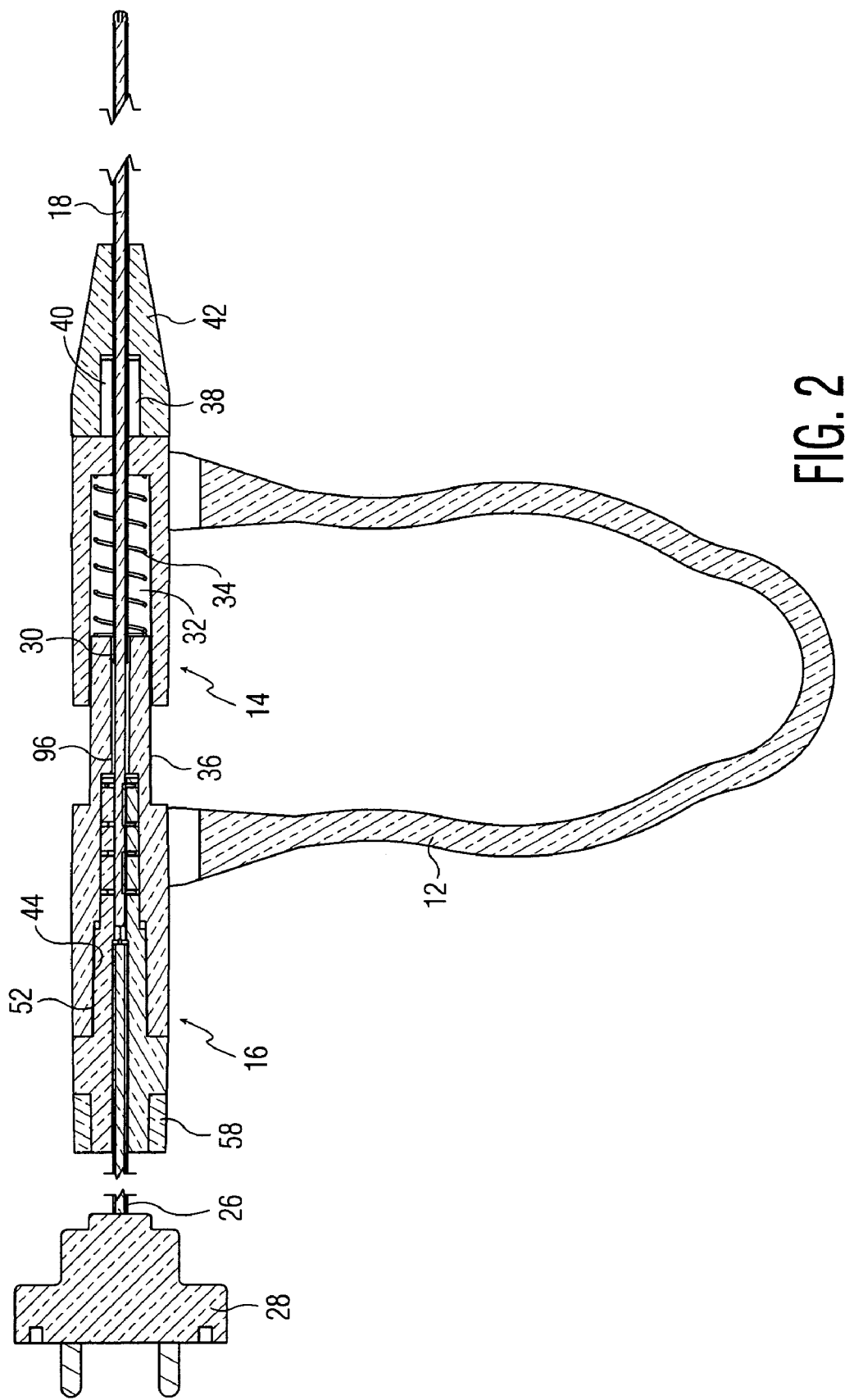
FIG. 2 is a vertical cross-sectional view of the electrosurgical handpiece of FIG. 1.
Figure 4:
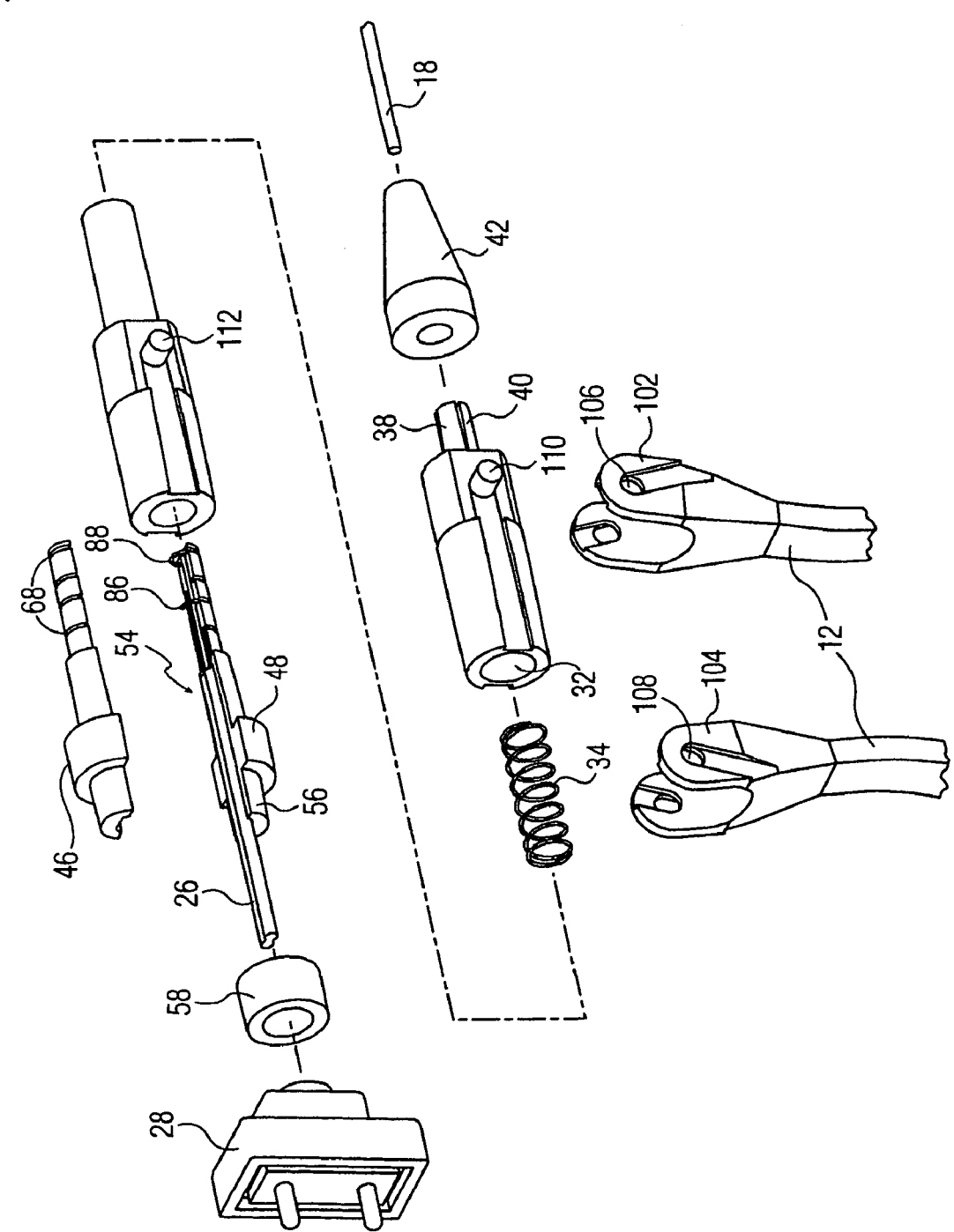
FIG. 4 is an exploded view of the electrosurgical handpiece of FIG. 1.

The cross-section of FIG. 2 shows the internal construction. The outer tubular housing 18 extends from the front at the right completely through the center of the front body part 14 and into the coaxially-aligned rear body part 16 and terminates in the latter where indicated at 30. The front body part 14 contains a bore 32 which houses a compression spring 34 engaged by a reduced diameter projecting member 36 of the rear body part 16. The compression spring 34 biases apart the two body parts 14, 16. The single-piece handle 12 prevents the body parts 14, 16 from coming apart. The front body part 14 also has a forwardly-projecting cylindrical collet 38 containing several longitudinal slits 40. Two of the slits are shown in FIG. 2, through which slits the cross-sectional view was taken which is why the slits are not hatched. Onto the forwardly-projecting collet 38 is mounted a nose piece 42 with an internal tapered bore (not shown) which is configured to cooperate in the conventional manner with the collet 38 so that when the nose piece is forced onto the forwardly-projecting collet 38, the collet part closes along the slits and locks to the outer tubular housing 18. In the embodiment shown, the nose piece 42 is permanently secured to the collet 38 so that the electrode is not changeable, but the handpiece construction can be modified to allow for a changeable outer tubular housing 18. This is easily accomplished by providing the collet 38 with outer screw threads and the nose piece bore with inner screw threads allowing the nose piece to be loosened for removal of the outer tubular housing 18, and replacement with another housing. In the exploded view of FIG. 4, only part of the electrical wire 26 is shown.

The rear body part 16 comprises a contact cap 44 made up of upper 46 and lower 48 cap parts. These two cap parts are essentially identical, each comprising a generally cylindrical body 50 with a central bore 52 (when assembled), a forwardly-projecting part 54, and a rearwardly-projecting part 56. The latter engages a collar member 58 which holds together the assembled parts. The forwardly-projecting part 54 comprises laterally-spaced axially extending grooves 60, 64, radial holes 66, and longitudinally-spaced circumferential grooves 68 which function to secure the end of the incoming wire 26 and make a reliable electrical surface contact between the active electrode and the wire ends. In a preferred embodiment for a bipolar construction, this is accomplished as follows (see FIGS. 6–9). The electrode 22 in this case is made, like the main body parts, of an electrically-insulating material, such as any of well-known moldable plastics. It can be divided into two internal compartments 70, 72 housing electrically-insulated wires 74 each connected to one of the active bipolar electrode tips 24. Openings 76 are provided at two longitudinally-spaced and laterally-spaced side portions of the tube 17 (only one of which is shown in FIG. 8, but both in FIG. 5), and then spaced electrically-conductive deposits or coatings 78 are made over each of the openings 76 so as to electrically contact, respectively, one of the internal wires 74. For example, the electrically-conductive deposits can be silvered coatings. The electrically-conductive coatings 78 also extend along the outer surface of the tube 22 to form two longitudinally-spaced electrically-conductive bands 78 that are exposed on the outer surface of the electrode tube 22. The arrangement is such that each of the external bands 78 forms an electrical contact to one of the internal wires 74. It will be appreciated that two electrically-insulated bands are required for providing separate electrical connections to each of the active bipolar tips. If a unipolar electrode were involved, then only one band would be required if only one internal wire 74 were present, which would then be connected to the unipolar electrode, or if two internal wires 74 were still present, then both could be internally interconnected to the single unipolar electrode, in which case the same dual band system could be employed but only one need be connected externally. Thus, with the two band arrangement illustrated, unipolar and bipolar electrodes could be interchanged and used with the same handpiece when the plug 28 is plugged into the proper socket of the electrosurgical equipment.

Figure 6:
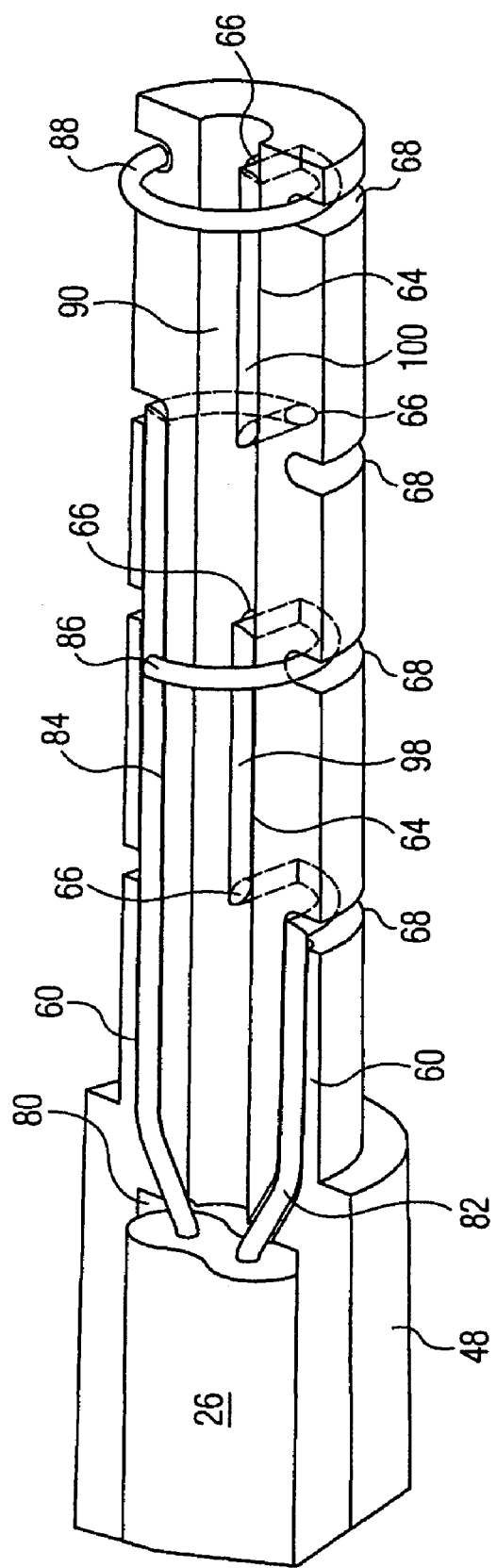
FIG. 6 is an enlarged view of part of the contact cap of the electrosurgical handpiece of FIG. 1.
Figure 7:
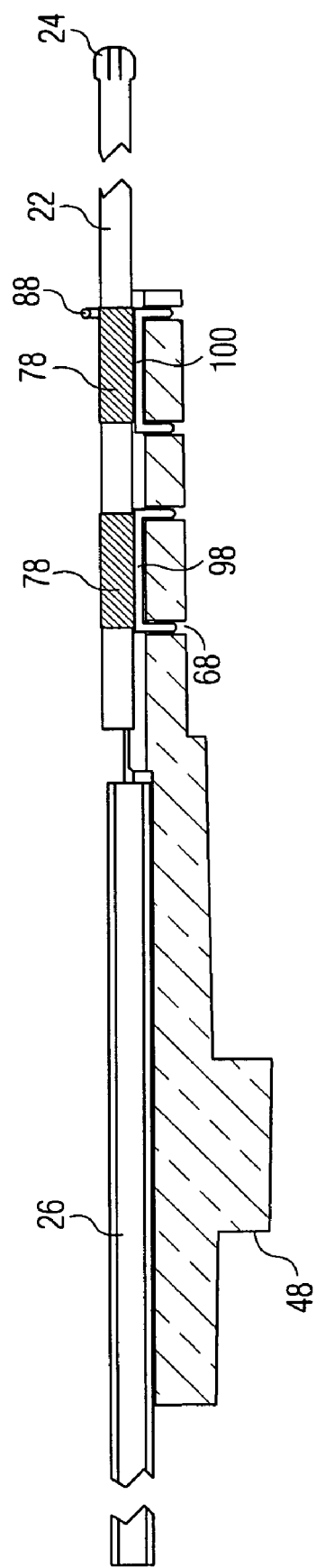
FIG. 7 illustrates how the contact cap makes electrical connections to the electrode tube housing.
Figure 8:
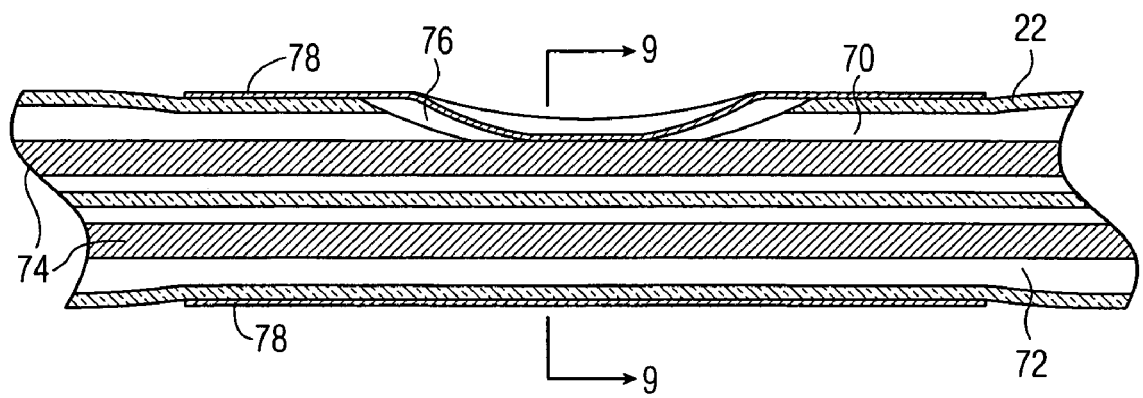
FIG. 8 is an enlarged cross-sectional view of part of the construction of the electrosurgical electrode used in the handpiece of FIG. 1 illustrating one way of making the contact surfaces on the electrode.
Figure 9:
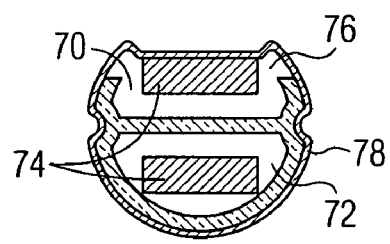
FIG. 9 is a cross-sectional view along the line 9—9 of FIG. 8.

The electrical connecting arrangement illustrated in FIGS. 6 and 7 is preferred because it allows for easy interconnections and assembly of the handpiece, without the need for welding or soldering operations. The insulated electrical wire 26 from the external plug 28 is laid into a groove 80 after the ends 82, 84 have been stripped of its insulation. One end 82 is placed inside the bottom groove 60 (in FIG. 6) which merges with the first annular external groove 68, makes a quarter turn in the latter groove and re-enters into the part 48 through the radial hole 66, runs axially forward inside the groove 64, exits through a radial hole 66 and makes another quarter turn in the second annular external groove 68 forming an end external circular portion 86 which extends above the lower cap 48 and eventually will be bent or folded into the corresponding second annular external groove 68 of the upper cap 46 when assembled to the lower cap 48. Similarly, the second end 84 is placed inside the upper groove 60 (in FIG. 6) which merges with the third annular external groove 68, makes a quarter turn in the latter groove and re-enters into the part 48 through the radial hole 66, runs axially forward inside the groove 64, exits through a radial hole 66 and makes in this case a full turn in the fourth or last annular external groove 68 forming an end external circular portion 88 which extends above the lower cap 48 and eventually will be bent or folded into the corresponding fourth annular external groove 68 of the upper cap 46 when assembled to the lower cap 48. The result of this arrangement is the partial exposure inside the assembled two cap halves of two spaced longitudinally-extending bare wire sections that are exposed to the bore interior 96. The first bare wire section 98 is connected to one of the 2-wire lead-in and the second bare wire 100 is connected to the second of the 2-wire lead-in. When the two cap parts are assembled, the bare wire sections remain exposed on the inside, and the assembly can be held together by addition of the end collar 58 and subsequent fusing if desired.

Now, when the electrode 18 is inserted axially along the aligned openings as shown in FIG. 7, the leading band 78 makes electrical contact with the longitudinally-extending wire section 100, and the trailing band 78 makes electrical contact with the longitudinally-extending wire section 98, thereby establishing a good electrical connection between the active bipolar tips 24 and the two wires of the lead-in conductor 26. Any electrode with a similar single or dual band arrangement can be used with the handpiece of FIG. 1, so long as it is configured so that it fits within the axially aligned bores and is provided with an external electrically-conductive band located to contact the internally exposed wire sections 98, 100. Note that, after assembly, the laterally-arranged stripped wire ends confined to their internal laterally spaced longitudinal grooves and longitudinally-spaced external annular or circumferentially-arranged grooves are completely electrically-insulated from one another producing internal (to the cap) longitudinally-spaced electrically-insulated wire sections 98, 100 which are easily contacted in a positive and reliable manner to the external bands on the removable or fixed electrode 18. One of the advantages of the arrangement described is that winding of the bare wire ends inside and around the various groves in the lower cap part 48 fixes the wires in place while the upper cap 46 is placed over the assembled lower cap and wire and the units held together at least temporarily by looping the respective wire ends 86, 88 into the corresponding grooves of the upper cap 46.

The assembly can be made permanent by force-fitting together of the parts or by using adhesives between the assembled parts. A preferred way is to slightly taper the various parts that telescope together, apply as by brushing to the eternal surface of the inner fitting part a suitable solvent for the plastic, and force the parts together. The solvent slightly dissolves a thin surface layer of the plastic and when the solvent evaporates, the two contacted parts are essentially fused together permanently.

As will be evident from FIG. 2, with the handle 12 removed, the two body parts 14, 16 separate. To complete the assembly, after the latter have been individually assembled, the spring 34 is inserted, and projecting part 36 assembled to the bore 32, the spring is then compressed, and the handle 12 mounted across the two body parts by means of the bifurcated ends 102, 104 with their respective holes 106, 108 engaging the posts 110, 112 on opposite sides of the two body parts 14, 16.

Figure 3:
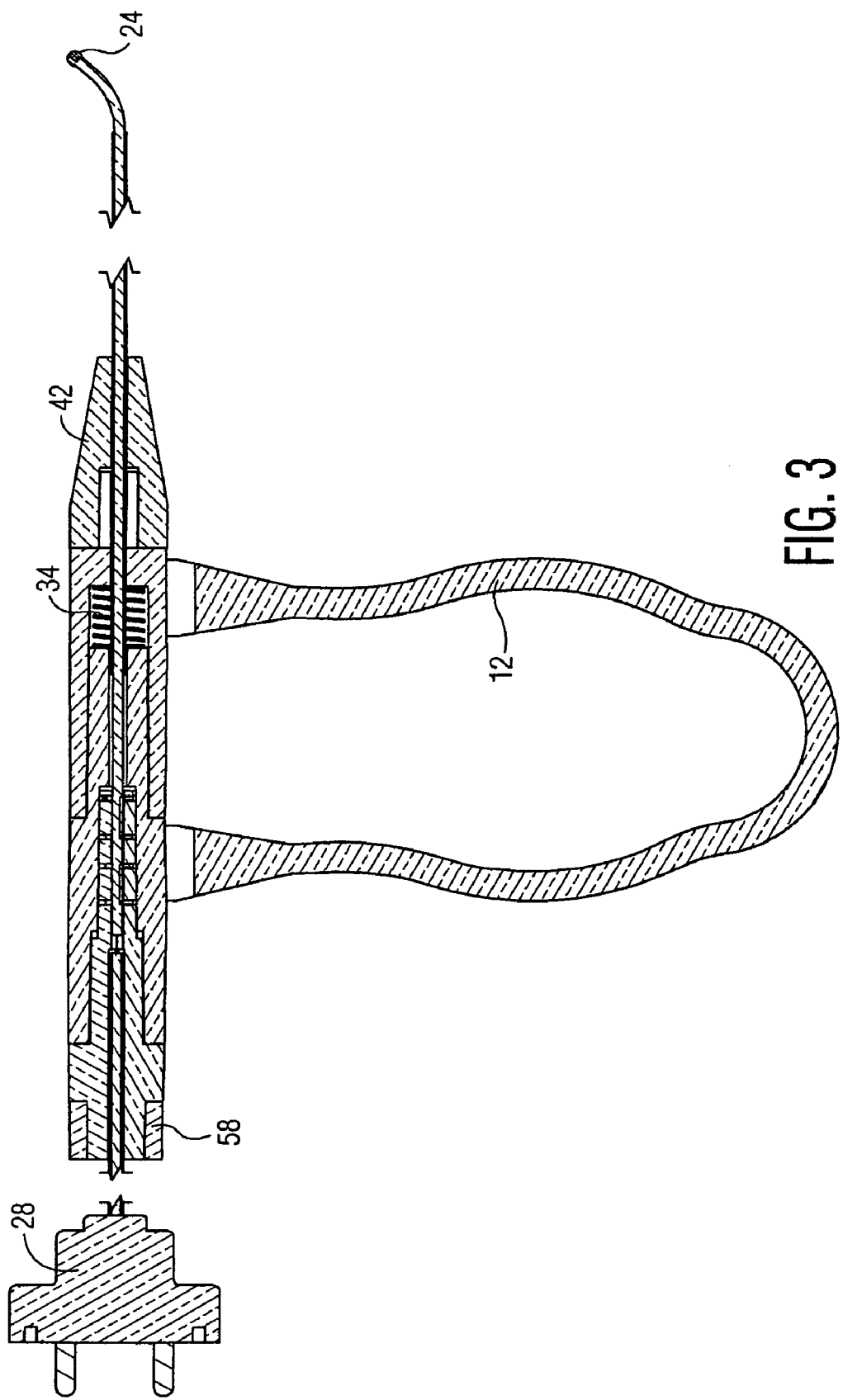
FIG. 3 is a vertical cross-sectional view of the electrosurgical handpiece of FIG. 1 but with the electrode extended into operating position.
Figure 5:
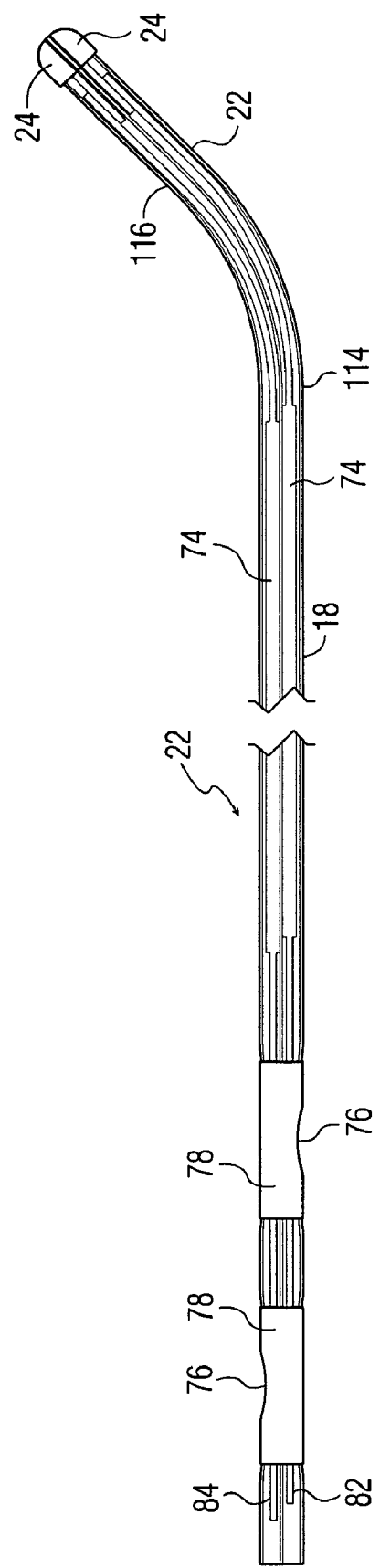
FIG. 5 is a partly cross-sectional view of the electrode tube housing of the electrosurgical handpiece of FIG. 1, also illustrating some of the electrical connections of the electrosurgical electrode used in FIG. 1.

FIG. 5 shows just the electrode tube 18 alone. The right end is referenced at 114, and 116 designates the extended active electrode with its bipolar tips 24 when the handle 12 is squeezed. The extended end 116 assumes a pre-bent shape or is constituted of memory metal, and when retracted slides smoothly back into the outer tube 18. (not shown in FIG. 5) FIG. 1 shows the assembled handpiece with a retracted electrode and FIG. 3 shows the arrangement when the handle is squeezed shut to extend the electrode. The bipolar tips or active unipolar end can be composed of any electrically-conductive metal, such as tungsten, steel, silver or silver alloys.

As in the earlier applications for the bipolar handpiece, two electrically-insulated wires are passed through insulated compartments of a tube. For a unipolar handpiece, only a single wire may be necessary connected to a typical unipolar electrode such as a ball, point, rod, or loop, as examples.

As used herein, by "axial" is meant parallel to the long axis of the electrode (horizontal in FIGS. 2 and 3). By "lateral" is meant transverse to the long axis of the electrode.

Once the surgeon has positioned the working end of the handpiece with respect to the tissue to be operated on, he or she then activates the electrosurgical apparatus causing a discharge of bipolar currents between the bare electrode loop ends 24 capable of causing ablation, shrinkage, or excision of tissue, or cauterization of a blood vessel in the usual way. Other usable mechanical or electrical structures following the teachings of the prior applications will be appreciated by those skilled in this art. As with the embodiments of the prior application, the insulating tube 18 will prevent accidental touching of patient tissue by the electrode sides, so that the bipolar discharge is localized to the spacing between the bare ends.

In all embodiments, the tubular housing 18 can be plastic, such as ABS or DELRIN, or of insulated relatively stiff metal that will not bend except where desired at the area of the openings 76. For example, the tube outside diameter can be typically about 0.04–0.1 inches. For the application of shrinking herniated tissue via a cannula, the tubular housing is typically about 15–20 inches long. It will also be noted that the features set forth in commonly owned U.S. Pat. Nos. 6,652,514 and 6,712,813, namely incorporating the handpiece with the flexible tip of the invention into the intelligent operating-mode selection system of the earlier patent, and/or as a procedure-dedicated handpiece of the later patent, can also be readily implemented by those skilled in this art following the teachings of those patents.

The automatic retraction of the electrode is caused in the preferred embodiment by the internal compression spring 34. Alternatively, the plastic handle can be configured such that it has built-in resilience which tends to return it to its open position shown in FIG. 1. As a further alternative, a resilient leaf or helical spring, for example, of metal or fiberglass, can be fitted inside of or between the handle sides to provide an outward bias force tending to maintain the handle sides in their open position. However, it is preferred that the handle itself be electrically-insulating to prevent any chance of an electric shock to the surgeon or the patient.

An important advantage of the construction described is its inexpensive construction and fabrication thus allowing handpiece disposability after one use. However, as explained above, the handpiece of the invention can also be reused if desired by appropriate sterilization after each use.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece comprising a squeezable handle (12) and a main housing including a distal tubular housing (18) and within the tubular housing (18) an elongated electrosurgical electrode (22) that can be selectively extended and retracted with respect to the distal end of the tubular housing (18) by squeezing the handle, characterized in that:

(a) the main housing comprises a first main body (14) and a second main body (16) located rearwardly of the first main body and longitudinally aligned with the first main body and slidingly coupled to the first main body, (b) the squeezable handle (12) being connected to and across the first and second main bodies such that, when the handle is unsqueezed, the first and second main bodies assume a first longitudinal position relative to one another, and when the handle is squeezed, the first and second main bodies assume a second longitudinally-displaced position relative to one another, (c) spring means (34) connected to and biasing the first and second main bodies into their first position, (d) the elongated electrosurgical electrode (22) having at its distal end an electrically-active part (24) and being connected to the second main body (16) for sliding movement therewith, the electrosurgical electrode (22) having an outer contact region (78) spaced rearwardly of its distal end and electrically-connected to its electrically-active part (24), (e) the second main body (16) having a forwardly-projecting part (54) coupled to the first main body (14) and comprising circumferential outer grooves (68) on the forwardly-projecting part, and axial inner grooves (64) on the forwardly-projecting part, (f) an electrical terminal means (26) at the rearwardly-located main body (16) and having bare wires (60) extending internally of the rearwardly-located main body, the bare wires having a portion located in the outer grooves on the forwardly-projecting part and a portion located in the inner grooves on the forwardly-projecting part and terminating internally in an exposed electrically-conductive region (98) such that the electrode contact region (78) is in electrical contact with the exposed electrically-conductive region (98) of the bare wires when the handpiece is in its assembled condition, (g) whereby, when the electrical terminal is activated and the handle squeezed, the first and second main bodies assume their second position and the electrically active part (24) of the electrode (22) is extended out of the distal end of the tubular first member (18) and is capable of supplying electrosurgical currents when applied to a patient.

2. An electrosurgical handpiece as claimed in claim 1, wherein the electrosurgical electrode is unipolar and has only one electrically active part, or the electrosurgical electrode is bipolar and has two electrically active parts.

3. An electrosurgical handpiece as claimed in claim 1, wherein the spring means comprises a compression spring mounted between the first main body and the second main body, or a band spring mounted to the handle, or the handle material itself.

4. An electrosurgical handpiece as claimed in claim 3, wherein both the electrical terminal (26) and the contact region (78) of the electrode are permanently connected to the second main body (16), and the tubular housing (18) is permanently connected to the first main body (14), the handpiece being disposable.

5. A disposable electrosurgical handpiece as claimed in claim 4, wherein the second main body (16) comprises a bore (26), the first main body comprises a bore (32) engaged from one side by the tubular housing (18) and from its opposite side by the forwardly-projecting part (54) of the second main body.

6. A disposable electrosurgical handpiece as claimed in claim 5, wherein the second main body (16) is in a telescoping relationship with the first main body (14), and the forwardly-projecting part (54) is in an adherent relationship with the second main body (16).

7. A disposable electrosurgical handpiece as claimed in claim 4, wherein the bare wires comprise two stripped ends (82, 84) forming longitudinally-spaced intermediate exposed electrically bare sections (98, 100) located between the outer grooves (68), the contact region of the electrode having two externally-exposed longitudinally-spaced contact surfaces (78).

8. A disposable electrosurgical handpiece as claimed in claim 4, wherein the internal grooves (60, 64) are connected to the external grooves (68) by a radial aperture (66).

9. A disposable electrosurgical handpiece as claimed in claim 4, wherein the second main body (16) is comprised of two interfitting halves forming the internal and external grooves.

10. A disposable electrosurgical handpiece as claimed in claim 4, wherein electrode (22) comprises an elongated insulating body and the contact region (78) comprises a conductive band formed on the outside of the elongated insulating body.

* * * * *